US006599354B1

(12) United States Patent
Schmalstieg et al.

(10) Patent No.: US 6,599,354 B1
(45) Date of Patent: Jul. 29, 2003

(54) PIPERAZINONE DERIVATIVES WITH ALKOXYSILANE GROUPS

(75) Inventors: Lutz Schmalstieg, Köln (DE); Ralf Lemmerz, Leverkusen (DE); Ulrich Walter, deceased, late of Langenfeld (DE), by Marie-Hélène Marie-Ange Christiane Walter, executor; Oswald Wilmes, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 27 days.

(21) Appl. No.: 10/019,583

(22) PCT Filed: Jun. 13, 2000

(86) PCT No.: PCT/EP00/05414

§ 371 (c)(1),
(2), (4) Date: Dec. 21, 2001

(87) PCT Pub. No.: WO01/00632

PCT Pub. Date: Jan. 4, 2001

(30) Foreign Application Priority Data

Jun. 25, 1999 (DE) .......................... 199 29 011
Jun. 25, 1999 (DE) .......................... 199 29 029

(51) Int. Cl.$^7$ .......................... C08G 77/26; C07F 7/18; C08L 83/00; C08J 3/100
(52) U.S. Cl. .................... 106/287.11; 524/588; 528/38; 544/229
(58) Field of Search .................. 544/229; 524/588; 528/38; 106/287.11

(56) References Cited

U.S. PATENT DOCUMENTS

| | | | |
|---|---|---|---|
| 2,971,864 A | 2/1961 | Speier | 117/124 |
| 3,470,255 A | 9/1969 | Kelly | 260/609 |
| 3,864,373 A | 2/1975 | Seler et al. | 260/448.8 R |
| 4,045,460 A | 8/1977 | Kleinstuck | 260/448.8 R |
| 4,234,503 A | 11/1980 | Kappler et al. | 556/413 |
| 4,481,364 A | 11/1984 | Chu et al. | 556/413 |
| 4,623,740 A | 11/1986 | Deschler et al. | 556/421 |

FOREIGN PATENT DOCUMENTS

| | | |
|---|---|---|
| DE | 115295 | 11/1900 |
| DE | 11 35 472 | 8/1962 |
| DE | 24 08 480 | 9/1975 |

OTHER PUBLICATIONS

J. Org. Chem. 36, Dec. 1971, pp. 3120–3126, John L. Speier C.A. Roth and John W. Ryan, Syntheses of (3–Aminoalkyl) silicon Compounds.
\*\*Chemical Abstracts, vol. 113, No. 7, Aug. 13, 1990, Columbus, Ohio, US; abstract No. 59818, Waldmann, H. et al.: "Synthesis of 2–acetamido–2–deoxyglucosyl". Seite 770; Spalte 2; XP002148061, Zusammenfassung & Carbohydr. Res., Bd. 196, Nr. 1, 1990, Seiten 75–93.

*Primary Examiner*—Emily Bernhardt
(74) *Attorney, Agent, or Firm*—Joseph C. Gil; Thomas W. Roy

(57) ABSTRACT

The present invention relates to new alkoxysilane-functional piperazinone derivatives, a process for their production, as well as their use as additives in sealants, adhesives, lacquers or coating agents.

4 Claims, No Drawings

PIPERAZINONE DERIVATIVES WITH ALKOXYSILANE GROUPS

BACKGROUND OF THE INVENTION

The present invention relates to new alkoxysilane-functional piperazinone derivatives, a process for their production, as well as their use as additives in sealants, adhesives, lacquers or coating agents.

Hydrolysable organofunctional silanes are important auxiliary substances in the formulation of sealants, lacquers or coating agents. An overview of the use of such compounds in the lacquer industry may be found for example in H. Kittel, Handbuch der Lacke und Beschichtungen [Manual of Lacquers and Coatings], S. Hirzel Verlag Suttgart, $2^{nd}$ Edition, 1998. Especially in all systems that crosslink via a silane polycondensation, aminofunctional silanes play an important role both as bonding agents and also as co-catalysts for the hardening. Alkoxysilanes containing amino groups are described for example in J. Org. Chem. 36 (1971), p. 3120, DE-A 11 52 95, 12 71 712, 21 61 716, 24 08 480, 25 21 399, 27 49 316 or U.S. Pat. Nos. 2,832,754, 2,971,864 or 4,481,364.

With aminofunctional silanes it is generally important that the compounds have on the one hand strongly polar amine groups that facilitate a good substrate bonding. On the other hand the aminofunctional silanes should not have too high a catalytic activity, so that they can also be used in relatively large amounts, which is always necessary when bonding to difficult substrates is required. When using relatively large amounts of aminosilanes belonging to the prior art, storage stability problems often arise due to the high catalytic activity of the aminosilanes.

The object of the present invention was accordingly to provide new aminofunctional silanes that facilitate a good bonding to various substrates and that can also be used in large concentrations without any problem. This object has been achieved with the alkoxysilane-functional piperazinone derivatives provided by the invention.

SUMMARY OF THE INVENTION

The invention provides piperazinone derivatives containing alkoxysilane groups of the general structural formula (I)

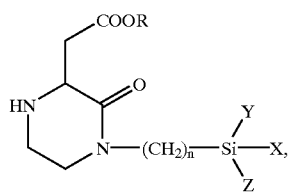

(I)

in which
R denotes a linear or branched alkyl radical with up to 12 carbon atoms,
X, Y and Z denote identical or different $C_1$–$C_4$ alkyl radicals or $C_6$ aryl radicals, with the proviso that at least one of these radicals denotes a $C_1$–$C_4$ alkoxy group, and
n denotes the number 2, 3 or 4.

The present invention also provides a process for the production of alkoxysilane-functional piperazinone derivatives of the formula (I)

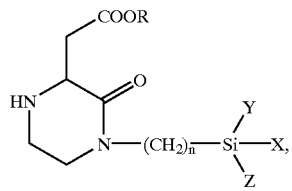

(I)

in which
R denotes a linear or branched alkyl radical with up to 12 carbon atoms,
X, Y and Z denote identical or different $C_1$–$C_4$ alkyl radicals or $C_6$ aryl radicals, with the proviso that at least one of these radicals denotes a $C_1$–$C_4$ alkoxy group, and
n denotes the number 2, 3 or 4,
characterised in that N-aminoethylaminoalkyl alkoxysilanes of the general formula (II)

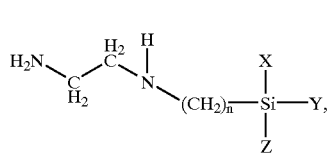

(II)

in which X, Y, Z and n have the meanings given in formula (I) are reacted with maleic acid esters and/or fumaric acid esters of the general formula (III)

  ROOC—CH=CH—COOR' (III), in which
R and R' independently of one another denote a linear or branched alkyl radical with up to 12 carbon atoms.

DETAILED DESCRIPTION OF THE INVENTION

In the aforementioned formulae n denotes the number 2, 3 or 4, preferably 3. X, Y and Z denote, independently of one another, alkyl radicals or alkoxy radicals with 1 to 4 carbon atoms, with the proviso that at least one of the radicals denotes an alkoxy radical; preferably all radicals X, Y, Z denote methoxy or ethoxy radicals. R and R' denote identical or different alkyl radicals with 1 to 12 carbon atoms, preferably identical radicals with 1 to 4 carbon atoms.

Examples of suitable N-aminoethylaminoalkyl alkoxysilanes are N-aminoethyl-3-aminopropyl-trimethoxysilane, N-aminoethyl-3-aminopropyl-triethoxysilane, N-aminoethyl-3-aminopropyl-methyldimethoxysilane or N-aminoethyl-3-aminopropyl-methyldiethoxysilane.

Examples of suitable maleic or fumaric acid esters are dimethyl maleate, diethyl maleate, dibutyl maleate, dioctyl maleate, didodecyl maleate, as well as the corresponding fumaric acid esters. Dimethyl maleate, diethyl maleate as well as dibutyl maleate are preferably used.

The reaction of the maleic or fumaric acid esters of the formula (III) with the N-ethylaminoalkyl alkoxysilanes of the formula (II) takes place within a temperature range from 0° to 140° C., preferably 40° to 100° C., the quantitative ratios generally being chosen so that the starting compounds are used in a molar ratio of about 1:1.

The reaction first of all involves an addition of the maleic or fumaric acid ester to the $NH_2$ group of the aminosilane within the meaning of DE-A 42 37 468, followed by a cyclocondensation reaction to form the piperazinone derivative with the elimination of the alcohol R—OH or R'—OH.

The reaction may be carried out in bulk or also in the presence of solvents, such as for example dioxane. The use of solvents is however less preferred. Mixtures of various N-ethylaminoalkyl alkoxysilanes may of course also be reacted with mixtures of fumaric acid esters and/or maleic acid esters.

The alcohol R—OH or R'—OH formed in the cyclocondensation reaction is as a rule removed from the reaction mixture by distillation. The alkoxysilane-functional piperazinone derivatives of the formula (I) according to the invention are colourless liquids that are obtained in such a high degree of purity after distilling off the alcohol R—OH or R'—OH that a distillative working-up is as a rule not necessary.

The present invention also provides for the use of the alkoxysilane group-containing piperazinone derivatives according to the invention of the formula (I) as additives and/or auxiliaries in lacquers, coatings, adhesives and sealants, preferably those that crosslink via a silane polycondensation.

The alkoxysilyl-functional piperazinone derivatives according to the invention are valuable additives for the production of lacquers, coatings, sealants as well as adhesives. On account of their chemical structure they facilitate on the one hand a chemical coupling to inorganic fillers and pigments via the alkoxysilyl groups, and on the other hand enable the polar piperazinone radical to bond well to a very wide range of substrates such as plastics materials, metals, mineral substrates or wood. The alkoxysilyl-functional piperazinone derivatives according to the invention may advantageously be used in particular in systems that crosslink via a silane polycondensation, such as for example silicones or alkoxysilyl-functional polyurethanes. In these systems the compounds according to the invention adopt not only the rôle of a bonding agent, but also have a particularly favourable catalytic activity. In systems that crosslink via a silane polycondensation, relatively large amounts of the compounds according to the invention may be used without there being any problem of storage stability.

EXAMPLES

Example 1

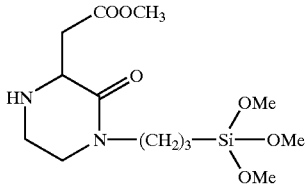

1 mole of N-aminoethyl-3-aminopropyltrimethoxysilane is placed in a reaction vessel at a temperature of 50° C. 1 mole of dimethyl maleate is then added dropwise while stirring, the temperature rising to 60° C. After the end of the dropwise addition the reaction mixture is stirred for 10 hours at 60° C. and 1 mole of methanol is then distilled off under a slightly reduced pressure. The reaction product is a pale yellow liquid with a GC purity of 95%. The band for the C=O vibration of the piperazinone ring appears in the IR spectrum at 1645 cm$^{-1}$. The band for the C=O vibration of the methyl ester radical appears at 1735 cm$^{-1}$. In the mass spectrum the polar molecule peak is observed at m/z=334. In the 1H-NMR spectrum the singlet for the methoxy protons of the ester radical is observed at 3.69 ppm, and the protons of the trimethoxysilyl group give rise to a singlet at 3.56 ppm.

Example 2

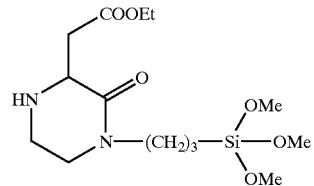

The procedure of Example 1 is adopted, except that diethyl maleate is used instead of dimethyl maleate. 1 mole of ethanol is distilled off under reduced pressure. The reaction product is a pale yellow liquid with a GC purity of 92%. The band for the C=O vibration of the piperazinone ring appears in the IR spectrum at 1650 cm$^{-1}$. The band for the C=O vibration of the ethyl ester radical appears at 1740 cm$^{-1}$. In the mass spectrum the polar molecule peak is observed at m/z=348.

Example 3

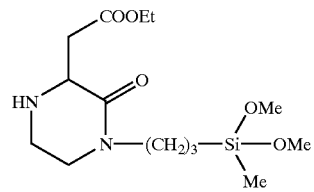

1 mole of N-aminoethyl-3-aminopropylmethyldimethoxysilane is placed in a reaction vessel at a temperature of 50° C. 1 mole of diethyl maleate is then added dropwise while stirring, the temperature rising to 60° C. After the end of the dropwise addition the reaction mixture is stirred for 10 hours at 60° C. and 1 mole of ethanol is then distilled off under a slightly reduced pressure. The reaction product is a pale yellow liquid with a GC purity of 93%. The band for the C=O vibration of the piperazinone ring appears at 1640 cm$^{-1}$ in the IR spectrum. The band for the C=O vibration of the ethyl ester radical appears at 1728 cm$^{-1}$. In the mass spectrum the polar molecule peak is observed at m/z=332.

Example 4

Production of a sealant based on a polyurethane containing alkoxysilyl terminal groups.

2000 g of a polyether diol having an OH number of 28, produced by propoxylation of propylene glycol and subsequent ethoxylation of the propoxylation product (PO/EO ratio=80:20) are prepolymerised with 155.4 g of isophorone diisocyanate at 70° C. with the addition of 0.02 g of dibutyltin dilaurate until the theoretical NCO content of 0.78% is reached. After cooling the reaction mixture to 60° C., 140.4 g of N-(3-trimethoxysilylpropyl)aspartic acid diethyl ester (prepared according to EP-A 596 360, Example 5) are quickly added dropwise and the reaction mixture is stirred until the isocyanate band can no longer be seen in the IR spectrum. The obtained polyurethane prepolymer containing alkoxysilyl terminal groups has a viscosity of 76000 mPas (23° C.).

The following components were processed in a commercially available planetary mixer to form a ready-for-use sealant:

| | |
|---|---|
| 36.4 parts by weight | polyurethane containing alkoxysilyl terminal groups |
| 12.9 parts by weight | diisoundecyl phthalate (plasticiser) |
| 0.02 part by weight | dibutyltin bis-acetoacetonate (10% dissolved in solvent naphtha 100) |
| 1.50 parts by weight | vinyltrimethoxysilane |
| 46.2 parts by weight | precipitated chalk (type: Socal U1S2) |
| 1.40 parts by weight | Disparlon ® NVG8403 S (thixotropic agent from Kusumoto Chem. Ltd.) |

The mixture is dispersed for 10 minutes at a pressure of 100 mbar, the internal temperature rising to 60° C.

3.0 parts by weight of alkoxysilyl-functional piperazinone derivative from Example 1 are then added and worked into the mixture by stirring for 10 minutes at a pressure of 100 mbar. The sealant produced in this way has an excellent storage stability, adheres to virtually all substrates, and hardens with a skin formation time of 30 minutes.

The product is packed in a commercially available cartridge dispenser and stored at 50° C. After a storage time of 90 days the product can still be processed without any problem and exhibits unchanged product properties.

The following mechanical properties were measured:

| | | |
|---|---|---|
| tensile strength: | 2.8 N/mm² | (DIN 53504) |
| elongation at break: | 315% | (DIN 53504) |
| tear propagation resistance: | 6.0 N/mm² | (DIN 53515) |
| Shore A hardness: | 40 | |

What is claimed is:

1. A piperazinone derivative containing alkoxysilane groups and corresponding to formula (I)

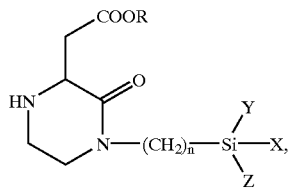

(I)

wherein
R represents a linear or branched alkyl radical with up to 12 carbon atoms,
X, Y and Z represent identical or different $C_1$–$C_4$ alkyl radicals or $C_6$ aryl radicals, provided that at least one of these radicals represents a $C_1$–$C_4$ alkoxy group, and n is 2, 3 or 4.

2. The piperazinone derivative containing alkoxysilane groups of claim 1 wherein X, Y and Z in each case represent methoxy radicals or ethoxy radicals.

3. A process for the production of the piperazinone derivative containing alkoxysilane groups of claim 1 which comprises reacting approximately equimolar amounts of an N-aminoethyl-aminoalkoxysilane of formula (II)

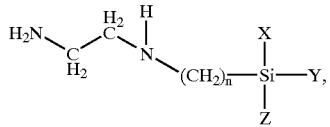

(II)

wherein X, Y, Z and n have the meanings set forth in formula (I) of claim 1, at a temperature range from 0° C. to 140° C. with a maleic acid ester and/or a fumaric acid ester of formula (III)

$$ROOC—CH=CH—COOR' \qquad (III),$$

wherein
R and R' independently of one another represent a linear or branched alkyl radical with up to 12 carbon atoms.

4. A coating, adhesive or sealant composition containing the piperazinone derivative containing alkoxysilane groups of claim 1.

* * * * *